(12) United States Patent
Pires et al.

(10) Patent No.: US 9,955,770 B2
(45) Date of Patent: May 1, 2018

(54) FLOCKED APPLICATOR

(71) Applicant: ZEN DESIGN SOLUTIONS LIMITED, Kowloon (HK)

(72) Inventors: Leo Clifford Pires, Basking Ridge, NJ (US); Roger Hwang, Maple (CA); Rahul Bose, New Delhi (IN); Smita Srivastava, New Delhi (IN)

(73) Assignee: ZEN DESIGN SOLUTIONS LIMITED, Kowloon, Hong Kong (CN)

( * ) Notice: Subject to any disclaimer, the term of this patent is extended or adjusted under 35 U.S.C. 154(b) by 221 days.

(21) Appl. No.: 14/745,865

(22) Filed: Jun. 22, 2015

(65) Prior Publication Data
US 2015/0374099 A1    Dec. 31, 2015

(30) Foreign Application Priority Data

Jun. 30, 2014 (IN) .......................... 1758/DEL/2014

(51) Int. Cl.
| | | |
|---|---|---|
| *A45D 33/00* | (2006.01) | |
| *A45D 40/26* | (2006.01) | |
| *A61F 13/40* | (2006.01) | |
| *B05D 1/00* | (2006.01) | |
| *A45D 33/36* | (2006.01) | |
| *A45D 34/04* | (2006.01) | |
| *A45D 40/00* | (2006.01) | |

(52) U.S. Cl.
CPC ........... *A45D 40/265* (2013.01); *A45D 33/36* (2013.01); *A45D 34/04* (2013.01); *A45D 34/045* (2013.01); *A61M 35/006* (2013.01); *B05D 1/007* (2013.01); *A45D 2040/0006* (2013.01); *A45D 2200/1018* (2013.01)

(58) Field of Classification Search
CPC .. A45D 34/046; A45D 34/045; A45D 40/267; A45D 33/36; A45D 34/042; A45D 40/262; A45D 40/265; A45D 2200/1009; A45D 2200/1018
USPC ...................................... 401/188 R, 126–135
See application file for complete search history.

(56) References Cited

U.S. PATENT DOCUMENTS

| | | | | |
|---|---|---|---|---|
| 4,861,179 | A * | 8/1989 | Schrepf ................ | A45D 40/265 132/218 |
| 5,551,456 | A * | 9/1996 | Hartel .................. | A45D 40/265 132/218 |
| 8,245,716 | B2 | 8/2012 | Malvar et al. | |
| 8,640,716 | B2 * | 2/2014 | Shimamura ............ | A45D 34/04 132/218 |
| 9,259,074 | B2 * | 2/2016 | Aso ...................... | A45D 34/046 |
| 9,398,800 | B2 * | 7/2016 | Uehara ................ | A45D 34/046 |
| 9,468,280 | B2 * | 10/2016 | Uehara ................ | A45D 34/045 |
| D787,191 | S * | 5/2017 | Hwang .......................... | D4/127 |

(Continued)

*Primary Examiner* — Jennifer C Chiang
(74) *Attorney, Agent, or Firm* — Patterson + Sheridan, LLP

(57) ABSTRACT

An applicator for applying a composition, such as makeup or a care product composition, e.g. lip gloss, mascara, eye liner, hair color, wound care, pharmaceutical or the like, that have diverse application characteristics. The applicator comprises an applicator element comprising a support and a layout of fibers on at least a portion of the support, the fibers being flocked to at least portion of the support and allow the applicator element to be loaded with the composition. The layout of fibers defines a pattern of fibers on the support and the pattern of fibers is visible to naked eye and perceptible to touch.

12 Claims, 7 Drawing Sheets

(56) References Cited

U.S. PATENT DOCUMENTS

| | | | | |
|---|---|---|---|---|
| 2003/0123919 A1* | 7/2003 | Gueret | A45D 34/00 | 401/130 |
| 2004/0009028 A1* | 1/2004 | Gueret | A45D 40/265 | 401/129 |
| 2006/0013639 A1* | 1/2006 | Gueret | A45D 34/045 | 401/130 |
| 2006/0272670 A1* | 12/2006 | Gueret | A45D 34/042 | 132/317 |
| 2007/0181143 A1* | 8/2007 | Montoli | A45D 40/262 | 132/320 |
| 2008/0083421 A1* | 4/2008 | Malvar | A45D 40/267 | 132/218 |
| 2009/0308309 A1* | 12/2009 | Aziz | B05C 17/00 | 118/264 |
| 2010/0303533 A1* | 12/2010 | Gueret | A45D 40/267 | 401/122 |
| 2011/0030716 A1* | 2/2011 | Lou | A45D 40/265 | 132/218 |
| 2011/0222955 A1* | 9/2011 | Thorpe | A45D 34/045 | 401/122 |
| 2012/0204899 A1* | 8/2012 | Uehara | A45D 34/045 | 132/320 |
| 2012/0219345 A1* | 8/2012 | Kim | A45D 40/26 | 401/126 |
| 2013/0343799 A1* | 12/2013 | Mitchell | A46B 9/005 | 401/126 |
| 2014/0037360 A1* | 2/2014 | Hofmann | A45D 40/265 | 401/129 |
| 2014/0290681 A1* | 10/2014 | Pires | A45D 34/045 | 132/200 |
| 2014/0348566 A1* | 11/2014 | Uehara | A45D 34/046 | 401/126 |
| 2014/0376988 A1* | 12/2014 | Fischer | A46B 9/021 | 401/129 |
| 2015/0182005 A1* | 7/2015 | Pires | A45D 40/267 | 401/122 |
| 2017/0071315 A1* | 3/2017 | Pires | A45D 34/04 | |

* cited by examiner

FLOCKED APPLICATOR

CROSS-REFERENCE TO RELATED APPLICATION

This application claims benefit of Indian Provisional Application Ser. No. 1758/DEL/2014, filed Jun. 30, 2014, which is incorporated by reference in its entirety.

BACKGROUND

Field of the Invention

The present disclosure relates to an applicator for applying a composition, such as a cosmetic or a personal care composition, to methods of making such an applicator and to packaging devices including such applicator. The disclosure relates more particularly to an applicator comprising an applicator element including a support and a layout of fibers defining a pattern on the support. The composition includes lip gloss, mascara, eye liner, hair color, wound care, pharmaceutical and like products.

Description of the Related Art

Conventionally, applicators for applying a composition such as lip gloss, mascara, eye liner, hair color, wound care, pharmaceutical and like products, comprise an elongated support with a multiplicity of fibers attached to the support by flocking process such that the fibers extend radially outwardly therefrom to form a fiber array surrounding the support over a substantial portion of a length of the support to form an applicator element/brush.

Flocking is a process whereby a surface is covered with more or less densely packed, upstanding fibers, typically of short length and fine diameter. The fibers typically are delivered to an adhesive coating already applied to the surface. One flocking method utilizes electrostatic delivery of fibers to the adhesive coating, although other procedures may also be employed. In conventional flocked applicators, the overall cylindrical and/or tapered profile of the fiber array is generally formed with an even distribution, density and length of fibers along the applicator element.

Some of such applicators known in the art include an applicator element configured to be connected at a distal end of a stem wherein the stem has a handle at its proximal end. Also, known in art are applicators having a flocked applicator element wherein the flocked applicator element is configured to be connected to a neck of a receptacle containing a composition. The composition flows from the receptacle towards the flocked applicator element either from its surrounding surface or through an aperture present in the applicator element.

US Pat. publication number 20120204899 discloses an applicator element having a support which has a concave surface. The concave surface is uniformly flocked with fibers of similar length so that the applicator element retains its concavity. The quantity of the cosmetic composition retained by the applicator element is increased because of the synergistic effect brought about by the combination of the curvedness of the applicator element and the effect of the flocking finish. The applicator element covered by a flocking provides a soft feeling when applied by a user.

U.S. Pat. No. 8,245,716 discloses flocked applicators having two types of bristles or fibers of different lengths. The flocked applicators disclosed in said patent comprises longitudinal voids which are devoid of flocking fibers. Such applicators are produced by masking the area of the applicator element with a sleeve and applying the fibers only on the unmasked areas. The unmasked areas may further be flocked by fibers of different length to achieve a pattern of fibers. Such applicators are difficult to manufacture because of many steps involved in the manufacturing process as they involve using a sleeve and applying different fibers at different steps of the process. The methods disclosed in the patent involve multiple steps and are too difficult to achieve the desired pattern.

There is a lot of scope for having a cosmetic applicator comprising an applicator element including a layout of fibers defining a pattern or a graphic print on flocked applicator element which may be visually attractive and can be used for marketing purposes.

The present disclosure further provides a cosmetic applicator having a flocked applicator element with at least one reservoir for retaining the composition.

The present disclosure further provides a cosmetic applicator having a flocked applicator element with fibers arranged in different patterns and which is easy to manufacture and is cost effective at the same time.

SUMMARY

Embodiments of the present disclosure generally relate to an applicator for applying a composition, such as makeup or a care product composition, e.g. lip gloss, mascara, eye liner, hair color, wound care, pharmaceutical or the like, that have diverse application characteristics.

According to another embodiment of the disclosure, the applicator comprises an applicator element having a layout of fibers defining a pattern or a graphic print on flocked applicator element which may be visually attractive and can be used for marketing purposes.

According to another embodiment of the disclosure, the applicator element comprises a support and a layout of fibers on at least a portion of the support, the fibers being flocked to at least portion of the support and allow the applicator element to be loaded with the composition. The layout of fibers defines a pattern of fibers on the support and the pattern of fibers is visible to the naked eye and perceptible to the touch.

According to another embodiment of the disclosure, the at least portion of the support before being flocked comprises a smooth and contiguous surface. The at least portion of the support before being flocked has no substantial surface features or the at least portion of the support is substantially even.

The term "no substantial surface features" or "substantially even" means that the features on the support do not represent themselves after the support is flocked. When the support with no substantial surface features or a surface which is substantially even is covered with flocking including solely substantially identical fibers, the surface of the flocked support may have no surface features or irregularities visible to the naked eye.

The layout of fibers defining a pattern of fibers on the support is the result of a treatment of fibers done after the support is flocked.

According to another embodiment of the disclosure, the layout of fibers defining a pattern comprises at least a first group of fibers and a second group of fibers wherein the first and the second group of fibers differ in their height as measured along an axis perpendicular to a longitudinal axis of the support.

According to another embodiment of the disclosure, the layout of fibers defining a pattern comprises at least a first group of fibers and a second group of fibers wherein the first group of fibers extends outwardly from the support and the second group of fibers is deformed in their structure.

According to another embodiment of the disclosure, the layout of fibers defining a pattern comprises at least a first group of fibers and a second group of fibers wherein the first group of fibers extends outwardly away from the support and the second group of fibers extends in a direction towards the support.

According to another embodiment of the disclosure, the layout of fibers defining a pattern comprises at least a first group of fibers and a second group of fibers wherein the first group of fibers extends outwardly from the support and the second group of fibers is pressed towards the support.

According to another embodiment of the disclosure, the layout of fibers defining a pattern comprises at least a first group of fibers and a second group of fibers wherein the first group of fibers extends outwardly in a direction perpendicular to a longitudinal axis of the support and the second group of fibers makes an angle other than 90 degree with respect to the longitudinal axis of the support.

According to another embodiment of the disclosure, the layout of fibers comprises at least a first group of fibers and a second group of fibers wherein the first group of fibers extends outwardly in a direction perpendicular to the longitudinal axis of the support and the second group of fibers are substantially parallel with respect to the longitudinal axis of the support.

As used herein, the term "substantially perpendicular" means that an angle is in the range of 45 to 135 degrees and the term "substantially parallel" means that an angle is in the range of 0 to 45 degrees.

According to another embodiment of the disclosure, there is provided a method of making the applicator of the present disclosure. The method involves following steps: Firstly, the fibers are flocked to at least a portion of the support, for example by electrostatic delivery of fibers to an adhesive coating located on the at least portion of the support. Such a method may cause the fibers being oriented substantially perpendicular to a plane/longitudinal axis of the support. The fibers may hence be distributed relatively uniformly over the adhesive-coated surface of the support. The application element covered with flocked fibers may therefore has substantially the same overall shape as that of the support before the support is covered with the flocked fibers, except, for example, for the added thickness of the flocked layer. However, other methods of flocking may also be used. While the fibers generally consist of soft and light material, stiffer fibers such as bristles may also be flocked.

Secondly, the flocked support is treated with at least one ornamental die having a raised pattern or a recessed portion so that the flocked support retains an imprint of the pattern of the ornamental die without any alteration in the substantially even surface of the support.

The pattern on the flocked support is the resultant of altering the effective height of at least one of the groups of fibers as measured along an axis perpendicular to the longitudinal axis/plane of the support, due to deformation of the at least one of the groups of fibers or due to change in direction of orientation of the at least one of the groups of fibers on the support.

The flocked support can be treated with the ornamental die in many ways as for e.g. the flocked support is contacted, while the adhesive is still wet, under pressure with the ornamental die containing a raised pattern or a recessed portion. The pressure from the raised pattern or the recessed portion of the ornamental die forces the fibers contacting the raised pattern or recessed portion down into the adhesive. The support can then be cooled and an embossed pattern results.

According to another embodiment of the disclosure, the flocked support is contacted, under pressure with a heated ornamental die containing a raised pattern or recessed portion. The heat and pressure from the raised pattern or recessed portion of the ornamental die results in altering the effective height of at least one of the groups of fibers, deforming the structure or changing direction of orientation of the at least one of the groups of fibers resulting in formation of a layout of fibers comprising at least a first group of fibers and a second group of fibers.

According to another embodiment of the disclosure, the support of the applicator element may have at least one planar surface.

According to another embodiment of the disclosure, the support may have an elongate shape defining an axis. The elongate shape may include, for example, one of a straight cylindrical shape, a curved cylindrical shape, a straight conical shape, a curved conical shape, a straight frustoconical shape, a curved frustoconical shape, a straight prismatic shape, a curved prismatic shape, feather-shape, rugby ball-shape, bean-shape, and spatula-shape.

According to another embodiment of the disclosure, the support may extend along a longitudinal axis that is entirely contained within a single plane. It would not be beyond the ambit of the present disclosure, if the longitudinal axis of the support is contained within more than one plane.

Further, the longitudinal axis of the support may be non-parallel to the longitudinal axis of the stem. Still further, the longitudinal axis of the support may cross the longitudinal axis of the stem at least once. According to another embodiment of the disclosure, the longitudinal axis of the support is curved.

According to another embodiment of the disclosure, the support may include at least one material selected from rigid materials, semi-rigid materials, thermoplastic materials, glass materials, metals, woods, flexible materials, and elastomers. The support may be porous, for example, so that it may be able to absorb at least some of the composition, which may provide a supply of the composition. The support may include magnetic and/or magnetizable materials, which may be coated, for example, with a silver resin. The fibers of the flocked support may include magnetic and/or magnetizable particles (e.g., a silver powder). The support may include a material which has a sufficiently high thermal inertia so that the composition is substantially prevented from cooling too quickly, for example, in the event that it is being applied after its temperature has been raised. The support may, for example, include a plastic material including a relatively high proportion of inorganic and/or other filler, for example, providing it with a relatively high heat capacity.

According to another embodiment of the disclosure, the fibers may include at least one material selected from polyamides, polyacrylics, polyesters, cottons, and cellulose. For example, the fibers may include at least one material selected from Nylon®, viscose, and rayon. The fibers may be selected from fibers having any colors.

According to another embodiment of the disclosure, the fibers may include straight fibers and curved fibers.

According to another embodiment of the disclosure, the fibers may be treated and/or include additives such as, for example, lubricating agents, absorbent agents, anti-UV agents, magnetic and/or magnetizable particles, and bactericidal agents, although the invention is not limited to these aforementioned additives.

According to another embodiment of the disclosure, there is provided a cosmetic applicator comprising a stem having a central longitudinal axis and having a distal end and a proximal end. The proximal end of the stem is connected to a handle while the distal end of the stem is connected to the applicator element.

According to another embodiment of the disclosure, there is provided a packaging device for applying a composition comprising a cosmetic applicator of the type described above and a receptacle containing a composition wherein the handle of the cosmetic applicator may function as a closure of the receptacle.

According to another embodiment of the disclosure, there is provided a cosmetic applicator comprising an applicator element wherein the applicator element is configured to be connected to a neck of a receptacle either directly or by a collar having a passageway for the composition to be delivered by the applicator element.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

Figure 1:
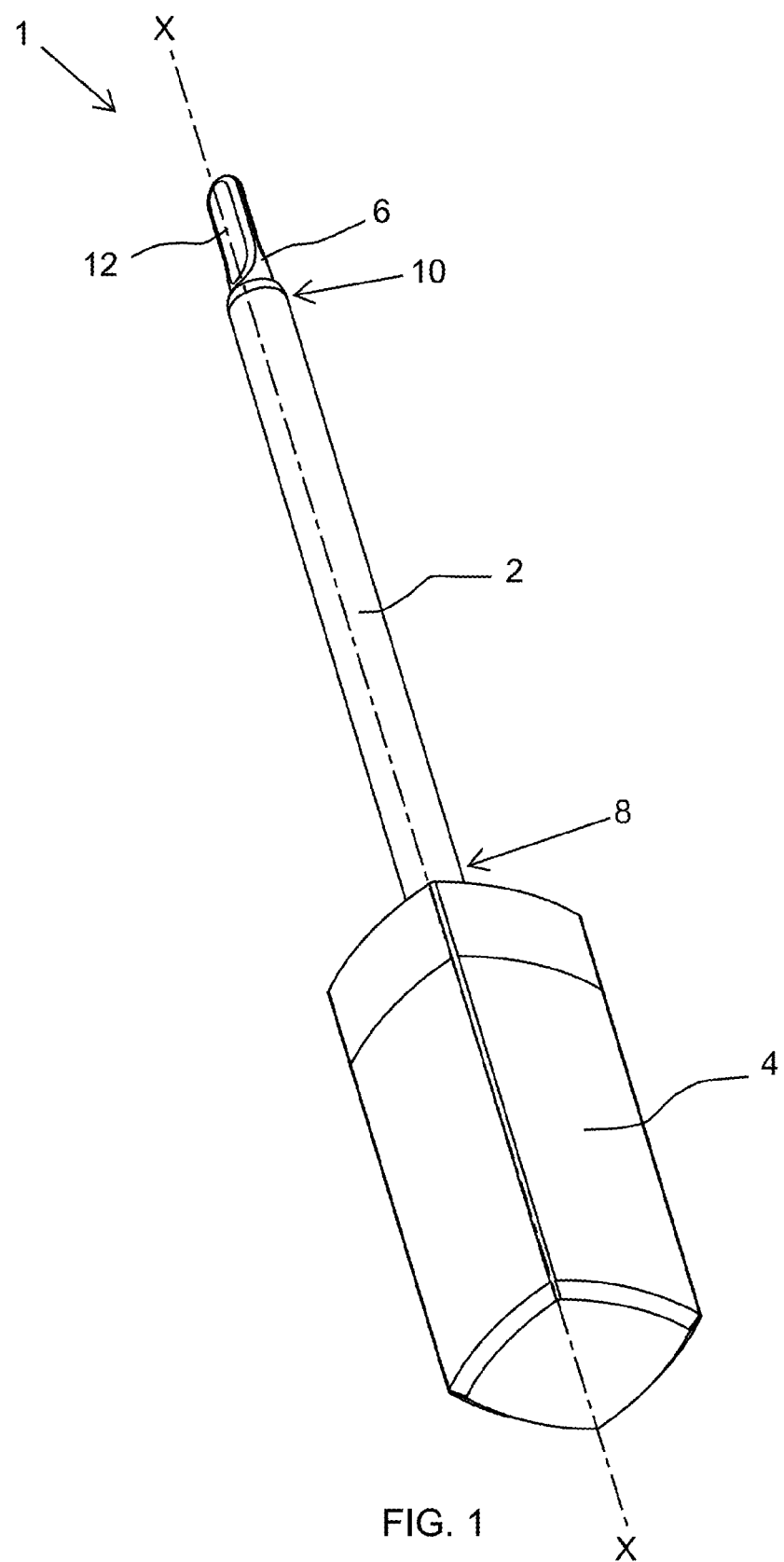
FIG. 1 illustrates an isometric view of an applicator according to an embodiment of the present disclosure.

To facilitate understanding, identical reference numerals have been used, where possible, to designate identical elements that are common to the Figures. It is to be noted, however, that the appended drawings illustrate only typical embodiments of this invention and are therefore not to be considered limiting of its scope, for the invention may admit to other equally effective embodiments.

DETAILED DESCRIPTION

An applicator 1 according to an embodiment of the present disclosure is shown in FIGS. 1 to 4. The applicator 1 may be used to apply a composition, such as a cosmetic or a personal care composition including lip gloss, mascara, eye liner, hair color, wound care, pharmaceutical and like products.

In an exemplary embodiment of the present disclosure, the applicator 1 is a lip applicator for applying lip gloss or other composition. In various other embodiments, the applicator 1 may be a face applicator, an eyeliner, mascara etc.

As shown in FIG. 1, the applicator 1 includes a stem 2, a handle 4 and an applicator element 6. Further, the applicator 1 extends along a longitudinal axis X-X. In an exemplary embodiment of the present disclosure, the stem 2 and the handle 4 may be substantially rigid members, whereas the applicator element 6 may be a rigid, semi-rigid or flexible member of the applicator 1. It may be contemplated that some or all parts, i.e., the stem 2, the handle 4 and the applicator element 6 of the applicator 1 may be manufactured separately and may be assembled together to form the applicator 1. Alternately, the stem 2 and the handle 4 can be manufactured as one part.

The stem 2 has a proximal end 8 and a distal end 10. The handle 4 may be attached to the proximal end 8 of the stem 2. In various embodiments, the proximal end 8 of the stem 2 may be attached to the handle 4 by using any type of locking mechanism known in the art, such as snap fit locking mechanism, threaded locking mechanism, etc. In another embodiment, the stem 2 and the handle 4 may be molded together as a single component of the applicator 1.

Further, the handle 4 may be detachably attached to a receptacle (not shown) containing a composition to form a packaging device (not shown) for the composition. In various embodiments, the handle 4 may be attached to the receptacle by any type of known locking mechanisms, such as snap fit locking mechanism, threaded locking mechanism, etc.

Further, the applicator element 6 is disposed at the distal end 10 of the stem 2. The applicator element 6 extends longitudinally along the longitudinal axis X-X of the applicator 1.

Figure 2:
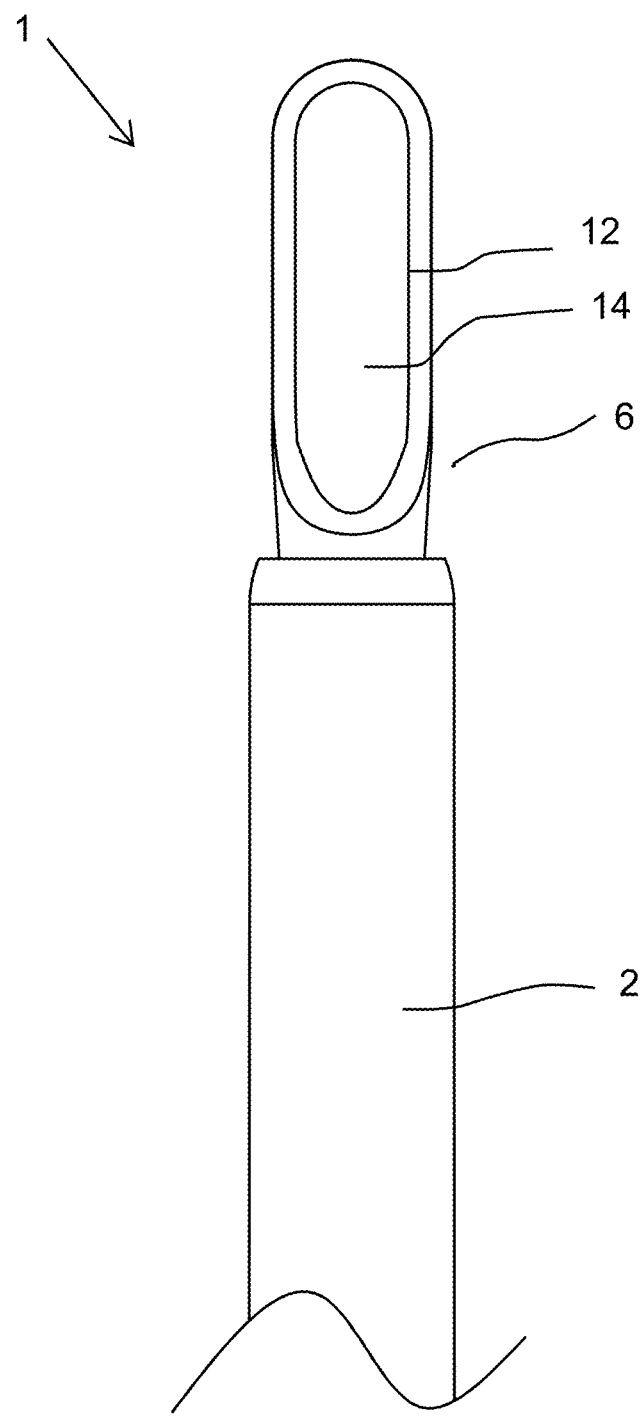
FIG. 2 illustrates a front view of a portion of the applicator of FIG. 1.

As shown in FIG. 2, the applicator element 6 includes a support 12. The support 12 is of a shape of a spatula. The support 12 may be obtained, for example, by molding it as a single piece with the stem 2. Alternatively, the support 12 may be snap-fastened, adhesively bonded, and/or welded to the stem 2.

At least a portion 14 of the support 12 comprises a smooth and a contiguous surface. The at least portion 14 of the support 12 has a planar surface. The term "planar surface" means a "flat surface". Further, the at least portion 14 of the support 12 has no substantial surface features or the at least portion 14 of the support 12 is substantially even.

The term "no substantial surface features" or "substantially even" means that the features if any on the portion 14 of the support 12 do not represent themselves after the support 12 is flocked. When the support 12 with no substantial surface features is covered with flocking including solely substantially identical fibers, the surface of the flocked support may have no surface features or irregularities visible to the naked eye.

Figure 3:
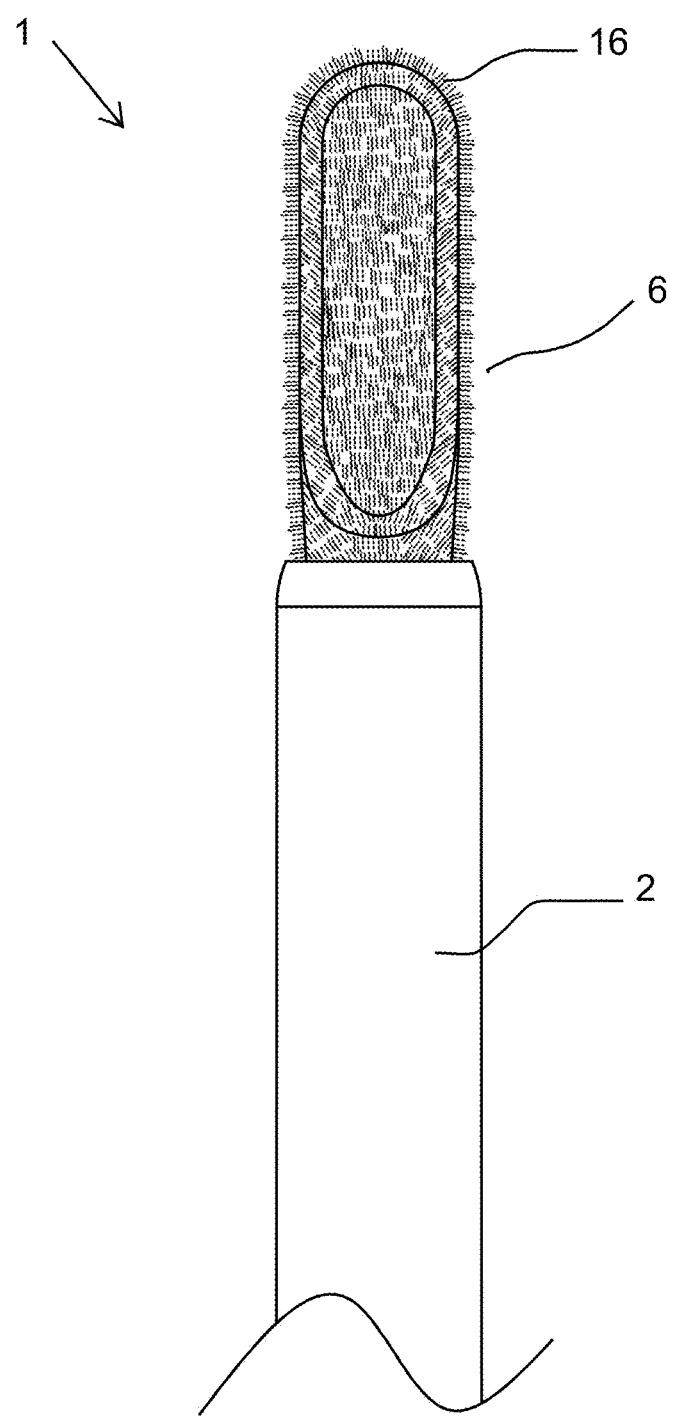
FIG. 3 illustrates a front view of a portion of the applicator of FIG. 1, after being flocked.

FIG. 3 shows the applicator element 6 having fibers 16 flocked on at least a portion 14 of the support 12 (shown in FIG. 2). The fibers 16 extend substantially perpendicular to a plane of the support 12.

As used herein, the term "substantially perpendicular" means that an angle is in the range of 45 to 135 degrees.

Figure 4:
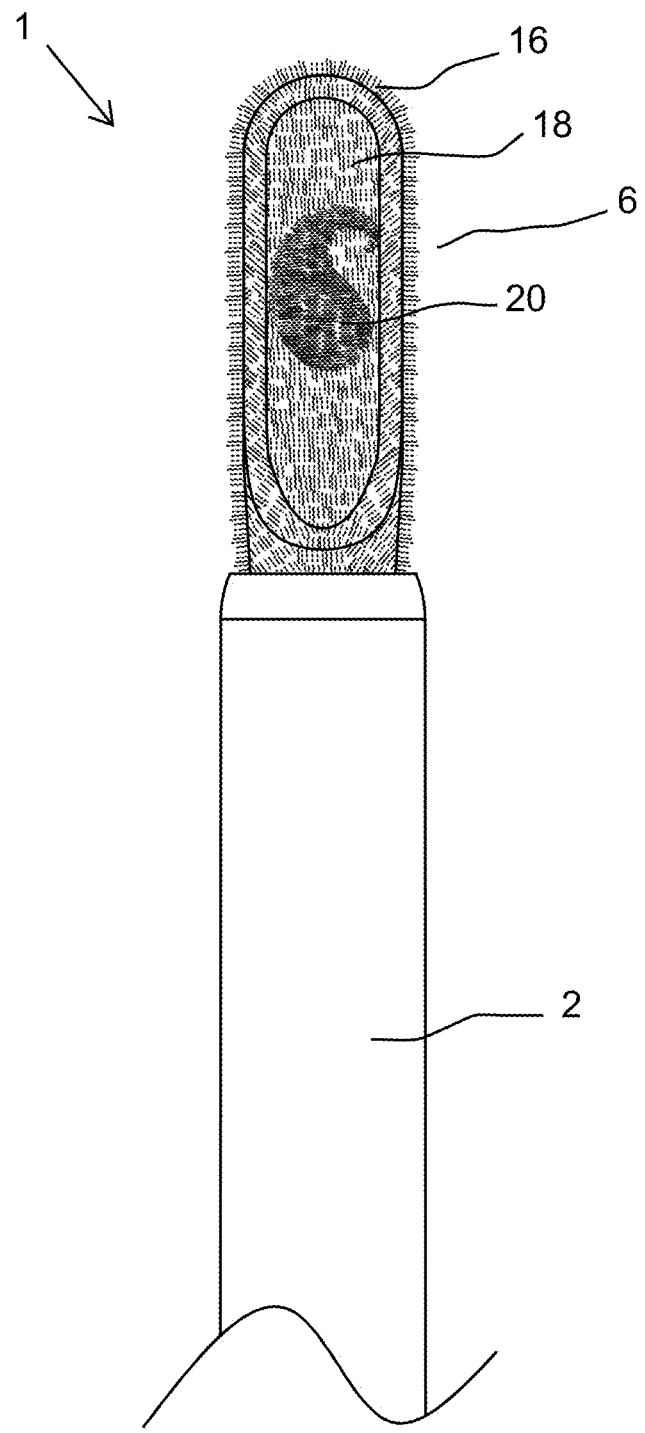
FIG. 4 illustrates a front view of a portion of the applicator after treatment of flocked applicator of FIG. 3.

FIG. 4 shows the applicator element 6 having a layout of fibers 16 defining a pattern or a graphic print on flocked applicator element 6 comprising at least a first group of fibers 18 and a second group of fibers 20 wherein the first group of fibers 18 extends outwardly from the support 12 and the second group of fibers 20 is deformed in their structure. The second group of fibers 20 is deformed in their structure as they are pressed towards the support 12. The second group of fibers 20 forms a reservoir or a cavity for holding the composition.

Also, FIG. 4 shows the first group of fibers 18 extends outwardly away from the support and the second group of fibers 20 extends in a direction towards the support. Alternatively, the first group of fibers 18 may extend outwardly in a direction perpendicular to the longitudinal axis of the support 12 and the second group of fibers 20 may be substantially parallel with respect to the longitudinal axis of the support 12.

As used herein, the term "substantially parallel" means that an angle is in the range of 0 to 45 degrees.

The applicator 1 shown in FIG. 4, having a layout of fibers 16 defining a pattern comprising at least a first group of fibers 18 and a second group of fibers 20 is formed by following steps:

Firstly, the fibers 16 are flocked to at least a portion 14 of the support 12 of applicator 1 in FIG. 2, for example by electrostatic delivery of fibers 16 to an adhesive coating located on the at least portion 14 of the support 12. Such a method cause the fibers 16 being oriented substantially perpendicular to a plane of the support 12. The fibers 16 may hence be distributed relatively uniformly over the adhesive-coated surface of the support 12 as shown in FIG. 3. The applicator element 6 covered with flocked fibers 16 may therefore has substantially the same overall shape as that of the support 12 before it is covered with the flocked fibers 16, except, for example, for the added thickness achieved by the length/height of the fibers 16 as measured along an axis substantially perpendicular to the longitudinal axis of the support 12. However, other methods of flocking may also be used. While the fibers 16 generally consist of soft and light material, stiffer fibers such as bristles may also be flocked.

Secondly, the support 12 covered with flocked fibers 16 is treated with at least one ornamental die (not shown) having a raised pattern so that the flocked support 12 retains the pattern of the ornamental die without any alteration in the substantially even surface of the support 12 wherein the pattern is defined by a first group of fibers 18 and a second group of fibers 20. Alternatively, the ornamental die may have a recessed portion.

The pattern comprising a first group of fibers 18 and a second group of fibers 20 on the flocked support 12, as shown in FIG. 4, is the resultant of altering the effective height of at least one of the groups of fibers 18, 20 as measured along an axis perpendicular to the longitudinal axis of the support 12, due to deformation of the at least one of the groups of fibers 18, 20 or due to change in direction of orientation of the at least one of the groups of fibers 18, 20 on the support 12. As specifically shown in FIG. 4, the effective height of the group of fibers 20 is altered as they are oriented in a direction towards the support 12 due to treatment of the fibers 16 with the ornamental die.

The flocked support 12 can be treated with the ornamental die (not shown) in many ways as for e.g. the flocked support 12 is contacted, while the adhesive is still wet, under pressure with the ornamental die containing a raised pattern. The pressure from the raised pattern of the ornamental die forces the fibers 16 contacting the raised pattern down into the adhesive. The support 12 can then be cooled and an embossed pattern comprising at least a first group of fibers 18 and a second group of fibers 20 results.

According to another embodiment of the disclosure, the flocked support 12 is contacted, under pressure with a heated die containing a raised pattern. The heat and pressure from the raised pattern of the ornamental die results in deforming the structure or changing in direction of orientation of some of the fibers 16 resulting in the group of fibers 20 which are oriented in a direction towards the support due to treatment of the fibers 16 with the ornamental die. This results in formation of a layout of fibers 16 defining a pattern of fibers comprising at least a first group of fibers 18 and a second group of fibers 20.

Figure 5:
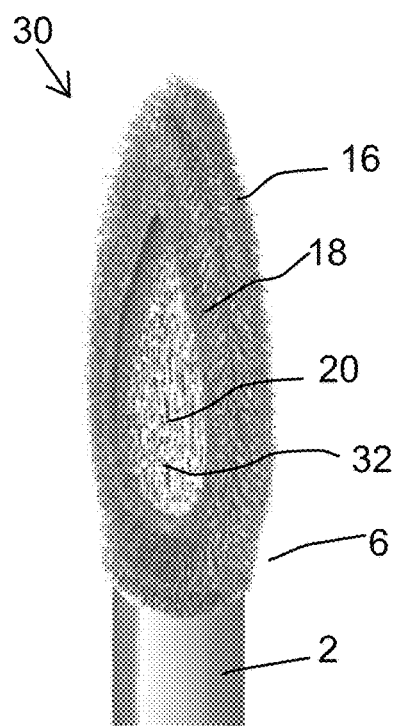
FIGS. 5-11 illustrate perspective views of portions of variant applicators according to other embodiments of the disclosure.
Figure 6:
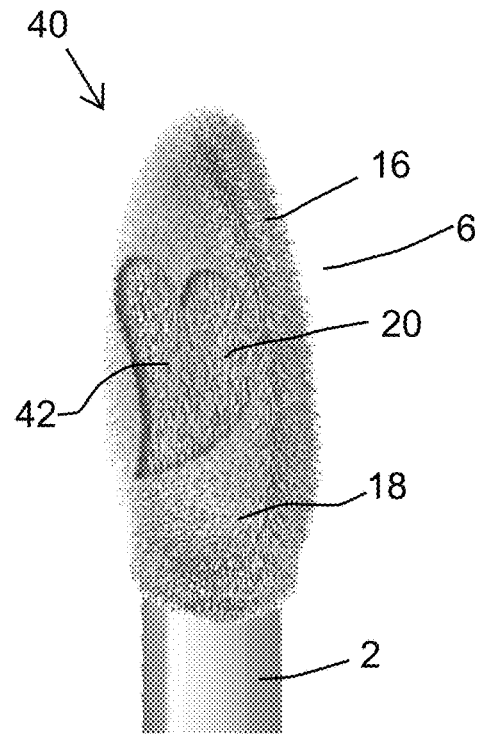

FIG. 5 and FIG. 6 show a portion of an applicator 30 and an applicator 40 respectively. Both the applicators 30 and 40 comprise an applicator element 6 and a stem 2. The applicators 30 and 40 are similar to the applicator 1 except, the shape of the applicator element 6 and the pattern defined by a layout of fibers 16 are different. However, the process used to achieve the pattern is similar to the process used for the applicator 1. The applicator 30 comprising an applicator element 6 has a layout of fibers 16 which define a pattern comprising a drop shaped reservoir 32 in center of the applicator element 6. The applicator 40 comprising an applicator element 6 has a layout of fibers 16 defining a pattern comprising a heart shaped reservoir 42 in center of the applicator element 6.

The pattern of fibers 16 achieved will depend on the raised pattern or recessed portion of the ornamental die.

FIG. 5 and FIG. 6 show the applicator 30 and 40 comprising a pattern of fibers 16 which further comprises a first group of fibers 18 and a second group of fibers 20 wherein the first group of fibers 18 has a height greater than the second group of fibers 20. Alternatively, the first group of fibers 18 extends outwardly from the support 12 (not visible as it is covered by the fibers) and the second group of fibers 20 is deformed in their structure. The second group of fibers 20 is deformed in their structure as they are pressed towards the support 12 (not visible as it is covered by the fibers). The second group of fibers 20 forms a drop shaped reservoir 32 in the applicator 30 and a heart shaped reservoir 42 in the applicator 40.

Figure 7:
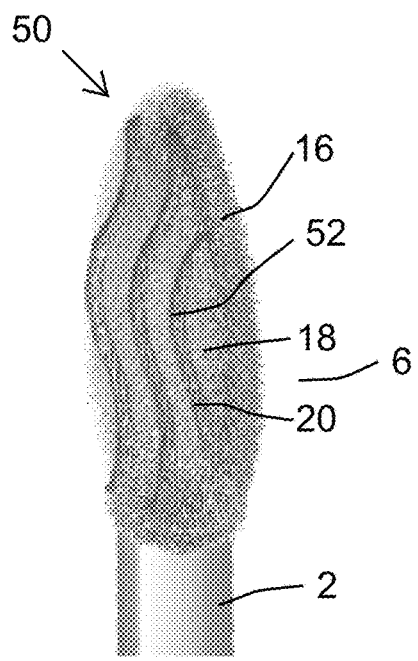
Figure 8:
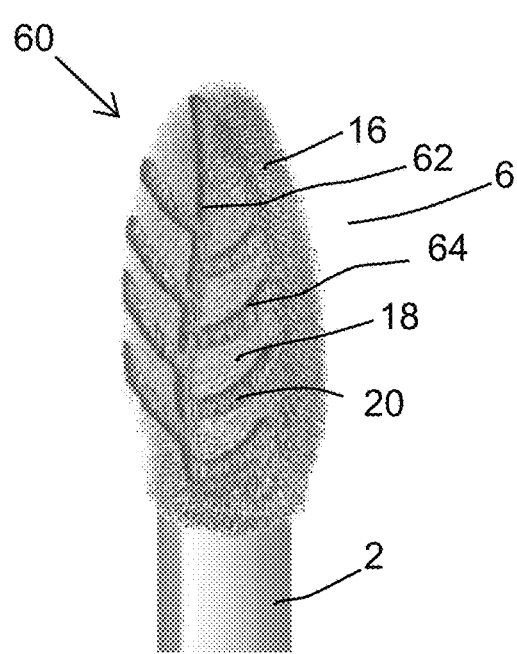

FIG. 7 and FIG. 8 show a portion of an applicator 50 and an applicator 60 respectively. Both the applicators 50 and 60 comprise an applicator element 6 and a stem 2. The applicators 50 and 60 are similar to the applicator 1 except, the shape of the applicator element 6 and the pattern defined by a layout of fibers 16 are different. However, the process used to achieve the pattern is similar to the process used for the applicator 1. The applicator 50 comprising an applicator element 6 has a layout of fibers 16 defining a pattern comprising a plurality of reservoirs 52 extending along whole length of the applicator element 6. The fibers 16 comprises a first group of fibers 18 and a second group of fibers 20 wherein the first group of fibers 18 has a height greater than the second group of fibers 20. The second group of fibers 20 is deformed in their structure as they are pressed towards the support 12 (not visible as it is covered by the fibers) and form the plurality of reservoirs 52. The applicator 60 comprising an applicator element 6 has a layout of fibers 16 defining a pattern comprising at least one reservoir 62 extending along whole length and along the central longitudinal axis of the applicator element 6 and a plurality of reservoirs 64 extending laterally from the reservoir 62. The reservoirs 62 and 64 forming a leaf like pattern on the applicator element 6.

Figures 9, 10:
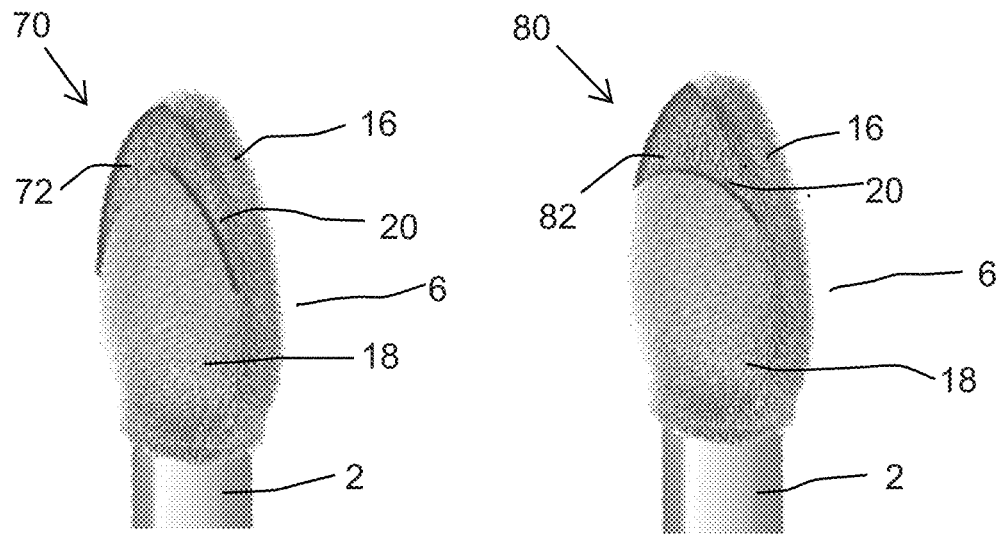
Figure 11:
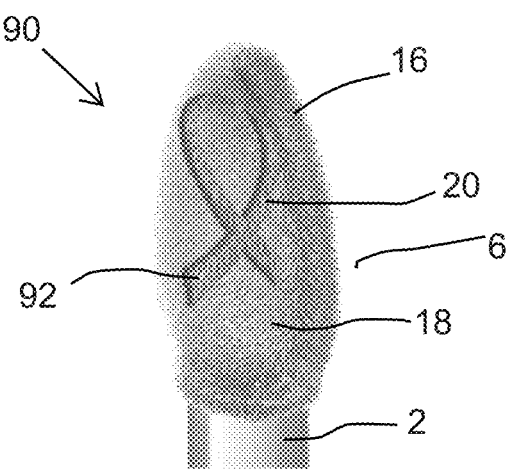

FIG. 9, FIG. 10 and FIG. 11 show a portion of an applicator 70, an applicator 80 and an applicator 90. These applicators are also similar to the applicator 1 except, the shape of the applicator element 6 and the pattern defined by a layout of fibers 16 are different.

Thus, by using the ornamental dies having variable raised patterns or recessed portions; it is possible to make applicators having a variety of patterns of flocked fibers.

Figure 12:
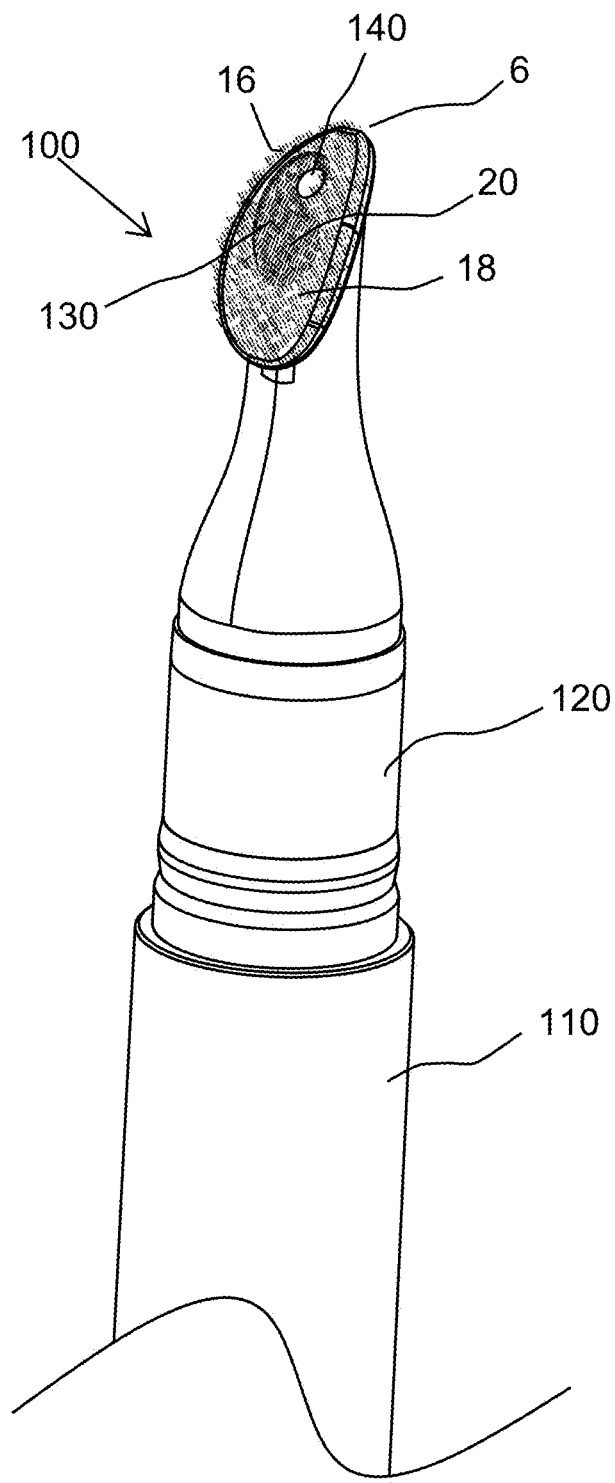
FIG. 12 illustrates a perspective view of an applicator connected to a receptacle according to a variant embodiment of the disclosure.

FIG. 12 shows an applicator 100 comprising a flocked applicator element 6 wherein the applicator element 6 is configured to be connected to a neck 120 of a receptacle 110 containing a composition (not shown). The composition flows from the receptacle 110 towards the flocked applicator element 6 through an aperture 140 present in the applicator element 6. The applicator element 6 having a layout of fibers 16 defining a pattern comprises at least a first group of fibers 18 and a second group of fibers 20 wherein the first group of fibers 18 extends outwardly from its support (not visible as it is covered by flocking) and the second group of fibers 20 is deformed in their structure. The second group of fibers 20 is deformed in their structure as they are pressed towards the support (not visible as it is covered by flocking). The second group of fibers 20 forms a reservoir 130 or a cavity for holding the composition.

Although the foregoing is directed to embodiments of the present invention, other and further embodiments of the invention may be devised without departing from the basic scope thereof, and the scope thereof is determined by the claims that follow. Accordingly, the appended claims should be construed to encompass not only those forms and embodiments of the invention specifically described above, but to such other forms and embodiments as may be devised by those skilled in the art without departing from its true spirit and scope.

What is claimed is:

1. An applicator for applying a cosmetic or a personal care composition, the applicator comprising:
   a stem having a central longitudinal axis and having a distal end and a proximal end, the proximal end of the stem is connected to a handle and the distal end of the stem is connected to an applicator element;
   wherein the applicator element comprises a support;
   wherein at least a portion of the support comprises a planar surface;
   wherein a plurality of fibers is flocked on the planar surface of the support,
   wherein the plurality of fibers defines a pattern of fibers on the planar surface of the support;
   wherein the plurality of fibers defining the pattern comprises at least a first group of fibers and a second group of fibers;
   wherein the first group of fibers extends outwardly from the support and the second group of fibers is pressed towards the support; and
   wherein the second group of fibers forms at least one cavity on the planar surface of the support for holding the cosmetic or the personal care composition.

2. The applicator according to claim 1, wherein the first group of fibers extends outwardly in a direction perpendicular to the support and the second group of fibers is substantially parallel with respect to the support.

3. The applicator according to claim 1, wherein the at least portion of the support before being flocked comprises a smooth and contiguous surface.

4. The applicator according to claim 1, wherein the pattern of fibers is visible to the naked eye and perceptible to the touch.

5. The applicator according to claim 1, wherein the applicator element comprises a plurality of cavities formed by the second group of fibers and the plurality of cavities extends along at least a major length of the applicator element.

6. The applicator according to claim 1, wherein the at least one cavity is formed at center of the support.

7. The applicator according to claim 1, wherein the applicator element comprises a plurality of cavities extending laterally from a central longitudinal axis of the applicator element.

8. The applicator according to claim 1, wherein the pattern formed by the first group of fibers and the second group of fibers defines a heart shaped cavity on the applicator element.

9. The applicator according to claim 1, wherein the pattern formed by the first group of fibers and the second group of fibers defines a drop shaped cavity on the applicator element.

10. An applicator for applying a cosmetic or a personal care composition, the applicator comprising:
    a stem having a central longitudinal axis and having a distal end and a proximal end, the proximal end of the stem is connected to a handle and the distal end of the stem is connected to an applicator element;
    wherein the applicator element comprises a support;
    wherein at least a portion of the support comprises a planar surface;
    wherein a plurality of fibers is flocked on at least a portion the planar surface of the support;
    wherein the plurality of fibers defines a pattern of fibers on the planar surface of the support;
    wherein the plurality of fibers defining the pattern comprises at least a first group of fibers and a second group of fibers;
    wherein the first group of fibers extends outwardly from the support and the second group of fibers is pressed towards the support;
    wherein the second group of fibers forms at least one cavity on the planar surface of the support for holding the cosmetic or the personal care composition;
    wherein the planar surface of the support before being flocked comprises a smooth and contiguous surface; and
    wherein the pattern of fibers on the support is a result of a post treatment of some of the plurality of fibers with an ornamental die, done after the support is flocked.

11. The applicator according to claim 10, wherein the plurality of fibers defines the pattern comprising at least a first group of fibers and a second group of fibers; and wherein the first group of fibers and the second group of fibers differ in their height as measured along an axis perpendicular to a longitudinal axis of the support.

12. An applicator for applying a cosmetic or a personal care composition, the applicator comprising:
    a flocked applicator element configured to be connected to a neck of a receptacle containing the cosmetic composition;
    an aperture in the flocked applicator element;
    wherein the cosmetic or the personal care composition flows from the receptacle towards the flocked applicator element through the aperture;
    wherein the flocked applicator element comprises a support;
    wherein at least a portion of the support has a planar surface and a plurality of fibers extends from the planar surface of the support;
    wherein the plurality of fibers comprises at least a first group of fibers and a second group of fibers;
    wherein the first group of fibers extends substantially perpendicular to the planar surface of the support of the applicator element;
    wherein the second group of fibers is pressed towards the planar surface of the support; and wherein the second group of fibers forms at least one cavity on the planar surface of the support for holding the cosmetic or the personal care composition.

* * * * *